(12) United States Patent
Kourogi et al.

(10) Patent No.: US 6,493,091 B2
(45) Date of Patent: Dec. 10, 2002

(54) INTERFERENCE DETECTING APPARATUS AND TOMOGRAPHY APPARATUS

(75) Inventors: Motonobu Kourogi, Kanagawa (JP); Motoichi Ohtsu, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 56 days.

(21) Appl. No.: 09/784,000

(22) Filed: Feb. 16, 2001

(65) Prior Publication Data

US 2001/0045513 A1 Nov. 29, 2001

(30) Foreign Application Priority Data

Feb. 18, 2000 (JP) ........................................ 2000-046831

(51) Int. Cl.[7] .............................................. G01B 9/02
(52) U.S. Cl. ....................................................... 356/489
(58) Field of Search ................................. 356/484, 489, 356/495, 512, 513, 514

(56) References Cited

U.S. PATENT DOCUMENTS 4,569,588 A * 2/1986 Nishiwaki et al. ......... 356/28.5
6,137,585 A * 10/2000 Hitzenberger et al. ...... 356/484

\* cited by examiner

*Primary Examiner*—Robert H. Kim
*Assistant Examiner*—Jurie Yun
(74) *Attorney, Agent, or Firm*—Oblon, Spivak, McClelland, Maier & Neustadt, P.C.

(57) ABSTRACT

Measurement of an internal structure of a sample is performed using interference of light within a short time. Through a first optical frequency comb generator 5 using a first signal having a frequency $f_1$ and generating reference light having a sideband every interval of the frequency $f_1$ and a second optical frequency comb generator 6 using a second signal having a frequency $f_2$ and generating object light having a sideband every interval of the frequency $f_2$, and sweeping of emission timing between the reference light and the object light, by changing a phase difference or frequency difference between the first signal and second signal, and detecting a change in light intensity of the interference light due to the interference, operation of detecting the interference position is made at a high speed.

5 Claims, 12 Drawing Sheets

INTERFERENCE DETECTING APPARATUS AND TOMOGRAPHY APPARATUS

BACKGROUND OF THE INVENTION

1. Field of the Invention

The present invention generally relates to an interference detecting apparatus and a tomography apparatus using interference property of light and detecting a structure of a measurement sample.

2. Description of the Related Art

A shape measuring apparatus employing light interference tomography is known as a measuring apparatus by which an internal structure, a refractive index, a thickness and so forth of an object is obtained.

As such a shape measuring apparatus, there is one shown in FIG. 14 for example. In this shape measuring apparatus, light L 101 emitted from a light source having a short coherence distance is split into object light L102 and reference light L103 by a beam splitter 102. The object light L102 is reflected by a measurement sample S via a scanner 103, thus becomes object light L104, and is incident on the beam splitter 102 again. Further, the reference light L103 is reflected by a reference-light mirror 105 positioned by a motor 106 via a frequency shifter 104, and is incident on the beam splitter 102 again.

The object light L104 and reference light L103 are combined as a result of being incident on the beam splitter 102, and then is incident on a photodetector 107 as interference light L105. The photodetector 107 detects the interference light in which light intensity is modulated through interference between the object light L104 and reference light L103, and generates a detection signal. The detection signal undergoes filtering, A/D (analog to digital) conversion, for example, by a signal processing circuit 108, and is input to a control part 109. In the control part 109, based on the input signal, an image indicating an internal structure of the measurement sample S, for example, is generated as a measurement result. Further, the control part 109 drives the motor 106 while controlling a motor control circuit 110 based on the input signal and a feedback signal from the motor 106. Further, the control part 109 controls the scanner 103 so as to cause it to scan the surface of the measurement sample S with the object light L102.

In this shape measuring apparatus, the measurement sample S is moved along Z directions or a reference mirror 105 is moved along X directions, and a distance the measurement sample S or reference mirror 105 has moved is obtained. Thereby, a distribution in reflectance of the measurement sample S along depth directions is obtained. Thereby, the shape measuring apparatus can perform tomographic measurement of the measurement sample S, and thereby, measures an internal shape and an external shape of the measurement sample S. This shape measuring apparatus can be used for observation of the inside of a living body by using light of a wavelength range of red through near infrared, for example.

Further, by the shape measuring apparatus in the prior art, when pulse laser is emitted as the light source 101 having a short coherent distance, it is possible to observe an internal structure of the measurement sample S by using a component thereof for which interference occurs as a result of the pulse reflected by the reference mirror 105 being on time.

However, in the shape measuring apparatus in the prior art, as the light source 101 is of a single one normally, it is necessary to control interference by mechanically controlling the position of the reference mirror 105 along the X directions. However, in many cases, as the movement speed of the reference mirror 105 has a limit, much time is required for measuring the measurement sample S.

Further, in the prior art, a tomography apparatus to which a method called Optical Frequency Domain Reflectometry: OFDR) is applied is proposed. However, actually, it is necessary to cause the frequency of a used laser to sweep through a wide range, and, mechanical driving is used for this purpose.

Further, in the prior art, there is an example without employing mechanical driving, which has, however, a low resolution.

SUMMARY OF THE INVENTION

The present invention has been proposed in consideration of the above-described situation, and an object of the present invention is to provide a shape detecting apparatus and a tomography apparatus by which it is possible to measure a sample within a short time at a high resolution.

An interference detecting apparatus relating to the present invention solving the above-described problems, comprises: a light source emitting light having coherency; a first signal generating means generating a first signal having a frequency of $f_1$; a first optical frequency comb generating means using the first signal provided from above-mentioned first signal generating means, modulating the light provided from the above-mentioned light source, and generating reference light having a sideband every interval of frequency $f_1$ in the light provided from the above-mentioned light source; a second signal generating means generating a second signal having a frequency of $f_2$; a second optical frequency comb generating means using the second signal provided from above-mentioned second signal generating means, modulating the light provided from the above-mentioned light source, and generating object light having a sideband every interval of frequency $f_2$ in the light provided from the above-mentioned light source; a combining means combining the reference light provided from the above-mentioned first optical frequency comb generating means and the object light generated by the above-mentioned second optical frequency comb generating means and reflected by a to-be-measured object so as to generate interference light; and a detecting means controlling an interference timing between the reference light provided from the above-mentioned first optical frequency comb generating means and the object light provided from the above-mentioned second optical frequency comb generating means, by using a phase difference or frequency difference between the first signal and second signal, and detecting a change in light intensity of the interference light.

A tomography apparatus relating to the present invention, comprises: in order to solve the above-described problems, a light source emitting light having coherency; a first signal generating means generating a first signal having a frequency of $f_1$; a first optical frequency comb generating means using the first signal provided from the above-mentioned first signal generating means, modulating the light provided from the above-mentioned light source, and generating reference light having a sideband every interval of frequency $f_1$ in the light provided from the above-mentioned light source; a second signal generating means generating a second signal having a frequency of $f_2$; a second optical frequency comb generating means using the second signal provided from the above-mentioned second signal generating means, modulating the light provided from the above-mentioned light source, and generating object light having a sideband every interval of frequency $f_2$ in the light provided from the above-mentioned light source; a combining means combining the reference light provided from the above-mentioned first optical frequency comb generating means and the object light generated by above-mentioned second optical frequency comb generating means and reflected by a to-be-measured object so as to generate interference light; a first detecting means controlling an interference timing between the reference light provided from the above-mentioned first optical frequency comb generating means and the object light provided from the above-mentioned second optical frequency comb generating means, by using a phase difference or frequency difference between the first signal and second signal, and detecting a change in light intensity of the interference light; a scanning means scanning the to-be-measured object with a position of application of the object light provided from the above-mentioned second optical frequency comb generating means; a second detecting means detecting shape information of the to-be-measured object based on an interference detection result given by the above-mentioned first detecting means; and an image producing means producing an image representing the shape of the to-be-measured object by using a plurality of shape information sets of the to-be-measured object generated by the above-mentioned second detecting means as a result of above-mentioned scanning means scanning it.

Other objects and further features of the present invention will become more apparent from the following detailed description when read in conjunction with the accompanying drawings.

DETAILED DESCRIPTION OF THE PREFERRED EMBODIMENTS

Embodiments of the present invention will now be described with reference to drawings.

Figure 1:
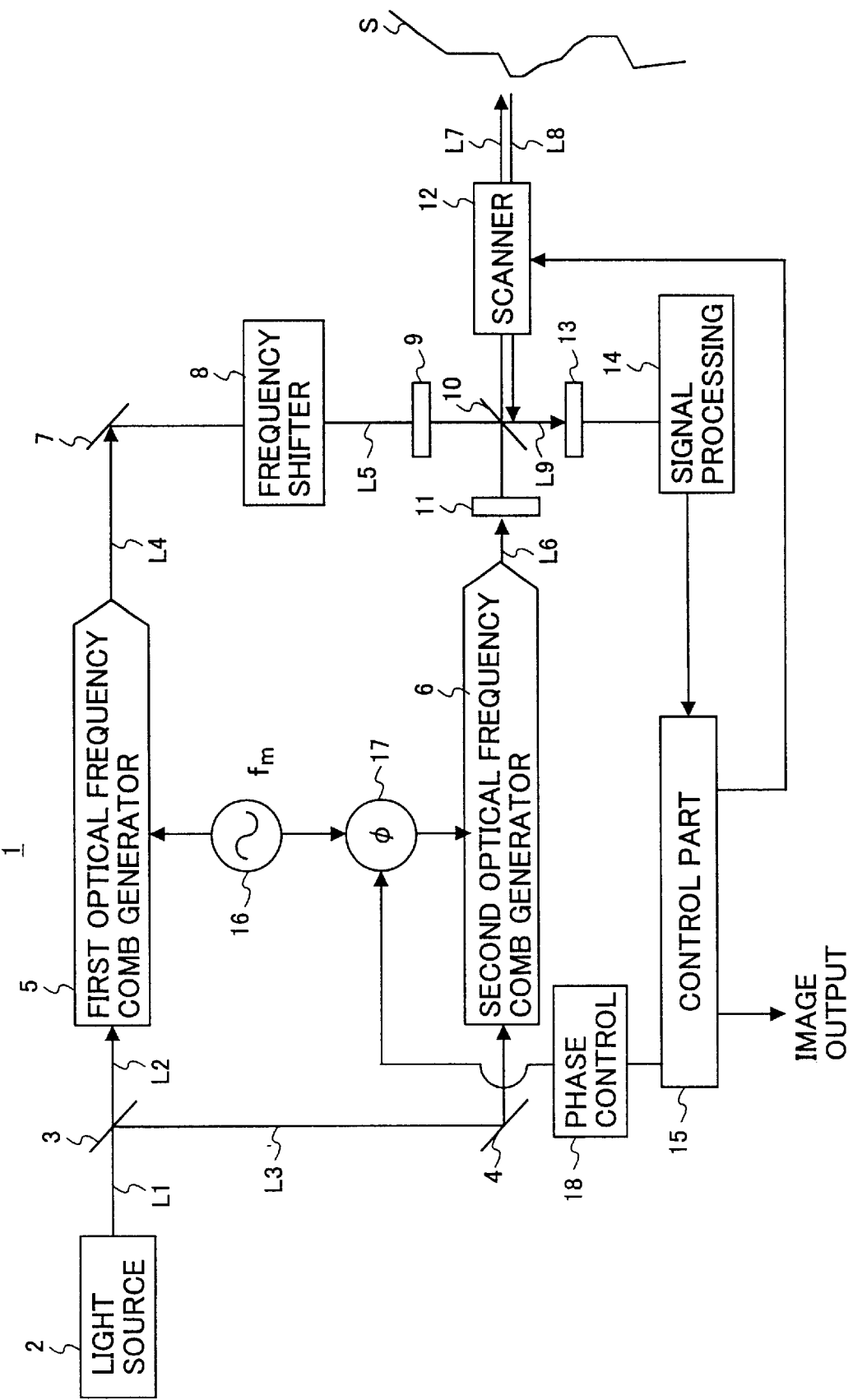
FIG. 1 is a block diagram showing a configuration of a tomography apparatus to which the present invention is applied.

A tomography apparatus 1 to which the present invention is applied is configured as shown in FIG. 1, for example.

The tomography apparatus 1 shown in FIG. 1 includes an optical system in which laser light from a light source 2 is incident on a first optical frequency comb generator 5 via a beam splitter 3, and on a second optical frequency comb generator 6 via the beam splitter 3 and a mirror 4. Then, light from the first optical frequency comb generator 5 is incident on a mirror 7, a frequency shifter 8, an isolator 9 and a beam splitter 10, and light from the second optical frequency comb generator 6 is incident on a measurement sample S via an isolator 11, a beam splitter 10 and a scanner 12. Then, light reflected by the measurement sample S is combined by the beam splitter 10, and then, is received by a photodetector 13. Further, this tomography apparatus 1 includes a signal processing part 14 and a control part 15 for obtaining a sample measurement result by using a light detection signal detected by the photodetector 13. Further, the tomography apparatus 1 includes an external oscillator 16 providing a first modulation signal to the first optical frequency comb generator 5 and a phase shifter 17 providing a second modulation signal to the second optical frequency comb generator 6. Further, the tomography apparatus 1 includes a phase control part 18 controlling the phase shifter 17.

The light source 2 generates the laser light L1 having coherency and a predetermined frequency, and emits it to the beam splitter 3.

The beam splitter 3 splits the laser light L1 into laser light L2 and laser light L3. This beam splitter 3 emits the laser light L2 to the first optical frequency comb generator 5, and emits the laser light L3 to the second optical frequency comb generator 6.

The external oscillator 16 includes an oscillator generating the first modulation signal having a frequency $f_m$. This external oscillator 16 provides the first modulation signal to the first optical frequency comb generator 5 and phase shifter 17.

The first optical frequency comb generator 5 has the laser light L2 incident thereon from the beam splitter 3, and, also, has the first modulation signal of the frequency $f_m$ input thereto from the external oscillator 16. This first optical frequency comb generator 5 includes, for example, an EOM (electro-optical modulator) and reflective mirrors disposed opposite so as to sandwich the EOM. The EOM and mirrors form a light oscillator. This first optical frequency comb generator 3 generates reference light in which the frequency of the incident laser light L2 is a central frequency $v_1$, and sidebands are generated with uniform intervals of the frequency $f_m$. As a result, the reference light has the sidebands having frequency components, i.e., $kf_m (k=-m, -m+1, m+2, \ldots, 0, 1, 2, \ldots, n)$ from the central frequency $v_1$.

Further, this first optical frequency comb generator 5 emits the reference light L4 as pulse light having predetermined timing according to a predetermined phase of the first modulation signal. This first optical frequency comb generator 5 emits the reference light L4 having the sidebands and of the pulse light to the mirror 7. The reference light L4 emitted from the first optical frequency comb generator 5 is then incident on the frequency shifter 8 via the mirror 7.

In the present embodiment, the reference light L4 emitted from the first optical frequency comb generator 5 is the pulse light, for example. However, it should not be the pulse light, but may be phase modulated light.

The frequency shifter 8 transmits the reference light L4 provided from the mirror 7, and, thereby, shifts each frequency component of the frequency $v_1+kf_m$ of the reference light L4 by Sf. As a result, the frequency shifter 8 causes each frequency component included in the reference light L4 to be $v_1+kf_m+Sf$, and then, emits it to the beam splitter 10. The frequency shifter 8 includes, for example, an AOM (Acoustooptic Modulator) which changes the phase of the reference light L4 through acousto-optical interaction by using an internally generated ultrasonic wave.

The phase shifter 17 has a phase control signal input thereto from the phase control part 18, and thereby, has the phase shifting amount φ thereof controlled. The phase shifter 17 shifts the phase of the first modulation signal provided from the external oscillator 16 by the phase shift amount φ.

Figure 2:
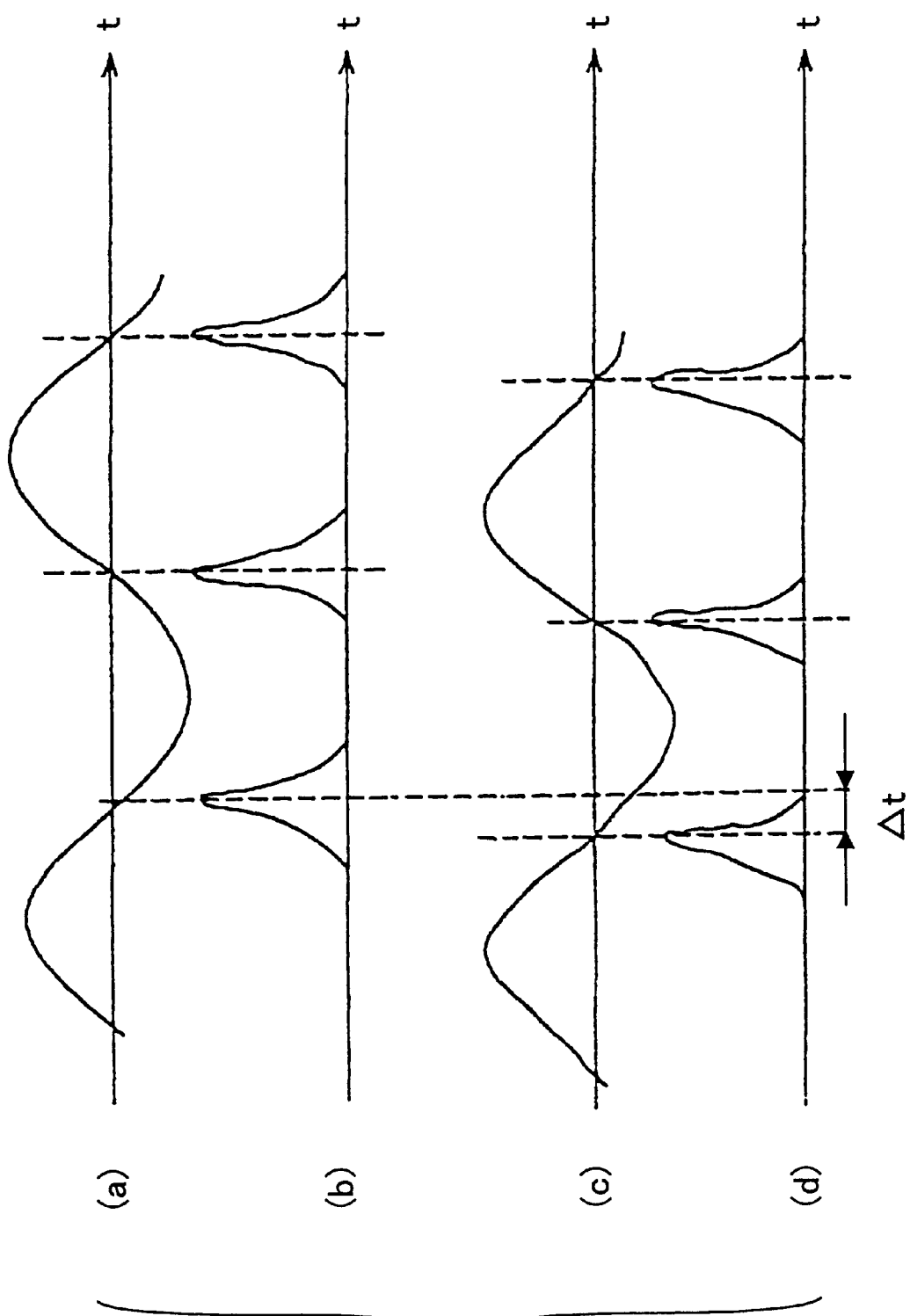
FIG. 2 (a) shows a change, with respect to time, in a first modulation signal, (b) shows a change with respect to time of an intensity of reference light emitted by a first optical frequency comb generator, (c) shows a change with respect to time of a second modulation signal and (d) shows a change with respect to time in intensity of object light emitted by a second optical frequency comb generator.

This phase shifter 17 controls the timing of object light L6 to be emitted from the second optical frequency comb generator 6. There, the reference light L4 and object light L6 are emitted at zero-crossing points of the first modulation signal and second modulation signal. This phase shifter 17 gives a time difference Δt in the timing between the reference light L4 (FIG. 2(b)) and object light (FIG. 2(d)) by giving the phase shift amount φ between the first modulation signal (FIG. 2(a)) and second modulation signal (FIG. 2(c)).

There, the time difference Δt between the timing the reference light L4 is emitted and the timing the object light L6 is emitted is expressed by $(\phi/2\pi) \times (1/f_m)$.

Further, the second optical frequency comb generator 6 makes the pulse light by controlling the timing of emitting the object light L6. This second optical frequency comb generator 6 emits object light L6 having sidebands for which a central frequency $v_2$ is regarded as a center, as pulse light, to the beam splitter 10. In the present embodiment, the object light L6 emitted from the second optical frequency comb generator 6 is the pulse light, for example. However, it should not be the pulse light, but may be any light as long as it causes interference with the reference light L4.

The isolator 9 transmits the reference light L5 provided from the frequency shifter 8 to the beam splitter 10. This isolator 9 has a function of transmitting light only in a direction directed from the frequency shifter 8 toward the beam splitter 10, and does not transmit light reflected by the beam splitter 10 and then incident on the first optical frequency comb generator 5.

The isolator 11 transmits the object light L6 provided from the second optical frequency comb generator 6 to the beam splitter 10. This isolator 11 has a function of transmitting light only in a direction directed from the second optical frequency comb generator 6 toward the beam splitter 10, and does not transmit light reflected by the beam splitter 10 and then incident on the second optical frequency comb generator 6.

The beam splitter 10 has the reference light L5 provided from the first optical frequency comb generator 5 incident thereon via the mirror 7 and frequency shifter 8, and, also, has the object light L6 provided from the second optical frequency comb generator 6 incident thereon. This beam splitter 10 transmits the object light L6 provided from the second optical frequency comb generator 6 toward the scanner 12. Further, the beam splitter 10 has object light L8 reflected by the measurement sample S incident thereon, and emits interference light L9 obtained through combination of the object light L8 provided from the scanner 12 and reference light L5, toward the photodetector 13.

The scanner 12 has the object light L6 provided from the second optical frequency comb generator 6 incident thereon via the beam splitter 10. This scanner 12 causes the object light L6 to scan the surface of the measurement sample S in accordance with the control signal given by the control part 15. Further, the scanner 12 has the object light L8 reflected by the inside of the measurement sample S incident thereon, and directs it toward the beam splitter 10.

The photodetector 13 has the interference light L9 provided from the beam splitter 10 incident thereon, and obtains a light detection signal according to the light intensity of the interference light L9. The photodetector 13 outputs the light detection signal obtained through the detection of the interference light L9 to the signal processing part 14.

The signal processing part 14 performs predetermined signal processing on the light detection signal given by the photodetector 13. The signal processing part 14 converts it into a direct-current signal through filtering and envelope detection, for example, performs A/D (analog to digital) conversion on the light detection signal, and generates a reflectance distribution signal indicating a reflection position of the object light L8 in the measurement sample S. The contents of processing performed by the signal processing part 14 will be described later.

Further, signal processing part 14 uses the light detection signal given by the photodetector 13, and performs spectrum analysis processing. This signal processing part 14 performs the spectrum analysis processing on the light detection signal given by the photodetector 13, thereby, detects the intensity of each frequency component included in the interference light L9, and outputs spectrum information indicating absorption for each frequency component, to the control part 15.

The phase control part 18 has the control signal given by the control part 15 input thereto. This phase control part 18 determines the phase shift amount φ of the phase shifter 17 based on the control signal given by the control part 15, and outputs the phase control signal to the phase shifter 17. Thereby, the phase control part 18 sets the phase shift amount φ of the phase shifter 17.

The control part 15 outputs the control signal to the phase control part 18, thereby changes the phase shift amount φ of the phase shifter 17, and controls the time difference Δt in timing between the reference light and object light. The control part 15 controls the phase control part 18 so as to change the phase shift amount φ continuously, and, thereby, changes the time difference Δt continuously so as to cause it to sweep.

The control part 15 has the reflectance distribution signal given by the signal processing part 14 input thereto, and generates shape information along depth directions of the measurement sample S. The control part 15 uses the shape information along the depth directions, and generates a sectional image indicating an internal structure of the measurement sample S.

Figure 3:
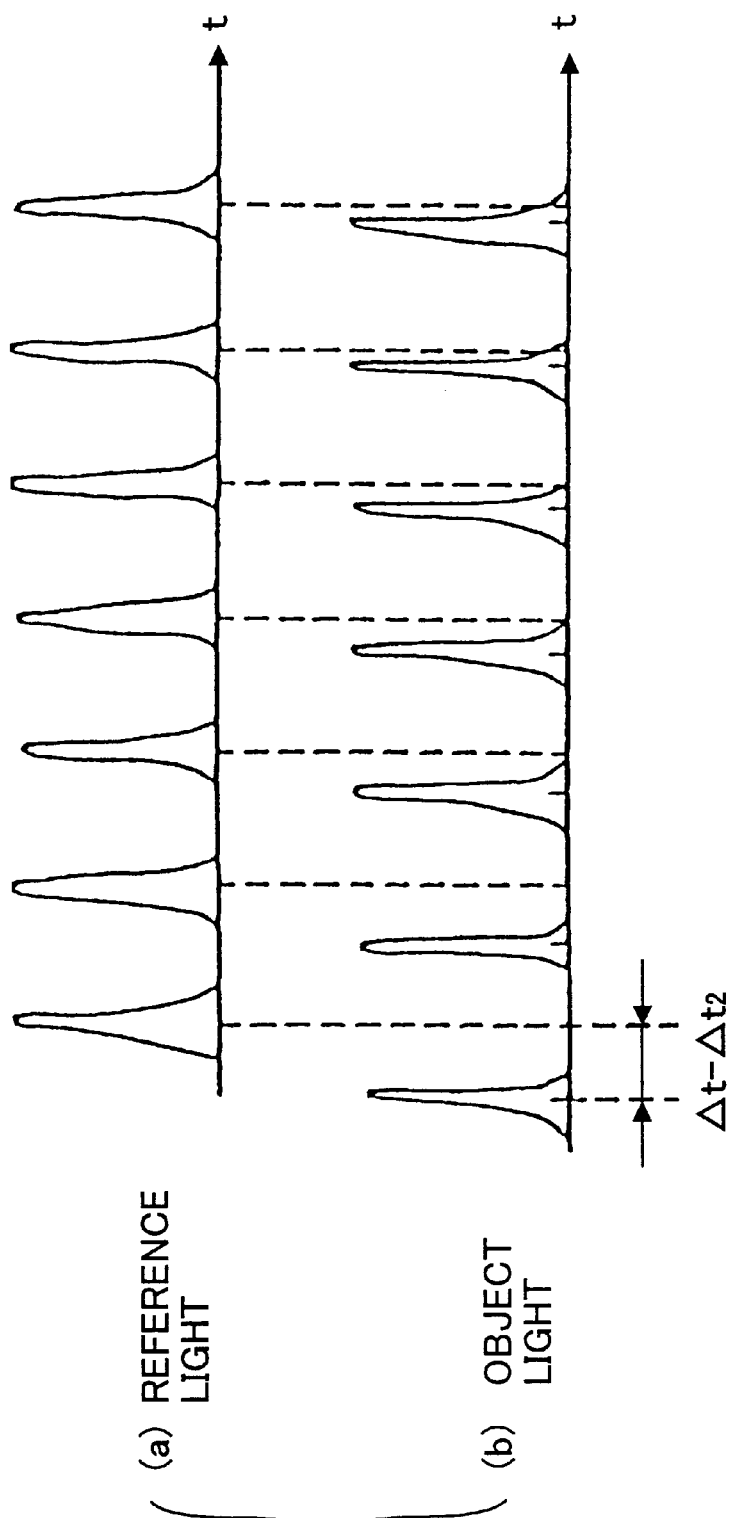
FIG. 3 (a) shows a change with respect to time of an intensity of the reference light and (b) shows a change with respect to time of an intensity of the object light.
Figure 4:
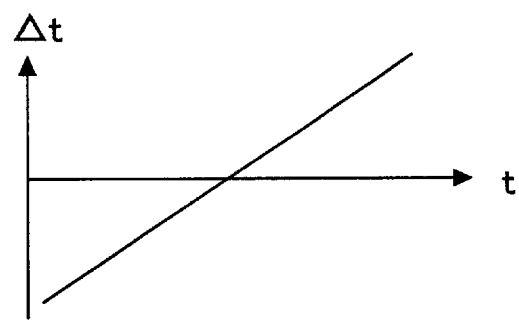
FIG. 4 shows a change with respect to time of a time difference $\Delta t$.

In the thus-configured tomography apparatus 1, for example, the reference light shown in FIG. 3(a) and the object light shown in FIG. 3(b) are combined, are incident on the photodetector 13, and the light detection signal in which the reference light shown in FIG. 3(a) and the object light shown in FIG. 3(b) are combined is input to the signal processing part 14. There, assuming that $\Delta t_2$ is a time difference between the reference light and object light due to delay time generated due to incidence of the object light onto the measurement sample S and then incidence thereof onto the beam splitter 10 again, the reference light (FIG. 3(a)) and object light (FIG. 3(b)) are incident with a time difference $\Delta t - \Delta t_2$. Further, as shown in FIG. 4, the reference light and object light are such that, as a result the phase shift amount $\phi$ being changed by the phase shifter 17, the time difference $\Delta t$ is changed depending on the time. The above-mentioned time difference $\Delta t - \Delta t_2$ is a time difference for the light emitted by the first optical frequency comb generator 5 and second optical frequency comb generator 6 to reach the photodetector 13, and differs according to the place at which the measurement sample S reflects the light.

A change with respect to time in electric field of the reference light generated by the first optical frequency comb generator 5 is expressed by the following formula (1), assuming that the frequency of the first modulation signal generated by the external oscillator 16 is $f_m$, when k is changed from −m to n, $$\sum_{k=-m}^{n} A_k \mathrm{Exp}[i2\pi(v_1 + kf_m + Sf)t] \quad (1)$$

A change with respect to time in electric field of the light generated by the second optical frequency comb generator 6 is expressed by the following formula in comparison to the formula (1) in the photodetector 13, assuming that the point at which the reflection by the measuring sample S is one point, the phase shift amount input from the phase shifter 17 for the second modulation signal with respect to the first modulation signal is $\phi$, the frequency of the second modulation signal provided to the second optical frequency comb generator 6 from the phase shifter 17 is $fm_2$, when k is changed from −m to n, and thus the sideband generated by the second optical frequency comb generator 6 is changed from −m to n, same as for the first optical frequency comb generator 5, $$\sum_{k=-m}^{n} B_k \mathrm{Exp}[i2\pi(v_2 + kf_{m2})(t - \Delta t_2)ik\phi + i\cos nt] \quad (2)$$

In the above formula (1), $A_k$(k=−m, −m+1, −m+2, ... n) denotes an optical complex amplitude of each frequency component included in the reference light. In the above formula (2), $B_k$(k=−m, −m+1, −m+2, ... n) denotes an optical complex amplitude of each frequency component included in the object light, i const denotes a value depending on the position of each optical component of the tomography apparatus 1. $v_1$ denotes the central frequency of the reference light. $v_2$ denotes the central frequency of the object light. When the light incident on the first optical frequency comb generator 5 and second optical frequency comb generator 6 is ones obtained from splitting the light emitted from the single light source 2, $\upsilon_1$ and $v_2$ have the same values.

The control part 15 causes the phase shift amount to sweep by controlling the phase control part 18, and, thereby, gives the phase shift amount $\phi$ to the reference light and object light through the phase shifter 17. Then, the control part 15 causes the reference light and object light to interfere one another, and obtains the light detection signal.

The light detection signal obtained when the reference light and object light interfere one another is expressed by:

$$|(\text{spectrum of reference light}) + (\text{spectrum of object light})|^2 \quad (3)$$

There, it is assumed that the upper limit of the detection band W of the photodetector 13 is such that $Sf < W < f_m$, and the direct-current component of the light detection signal obtained by using the above formula (3) is cut off. Then, the light detection signal results in a signal having a waveform shown in FIG. 5. There, the light detection signal shown in FIG. 5 has the following value, when k is changed from −m to +n:

$$\mathrm{Re}\left[\sum_{k=-m}^{n} A_k B_k * \right.$$
$$\left. \mathrm{Exp}(i2\pi Sft + i2\pi v \Delta t_2 + i2\pi k f_m \Delta t_2 - ik\phi + i\cos nt)\right] \quad (4)$$

There, in the formula (4), as $v_1 = v_2$, they are simply written as v, and, as $f_{m1} = f_{m2}$, they are simply written as $f_m$.

Figure 5:
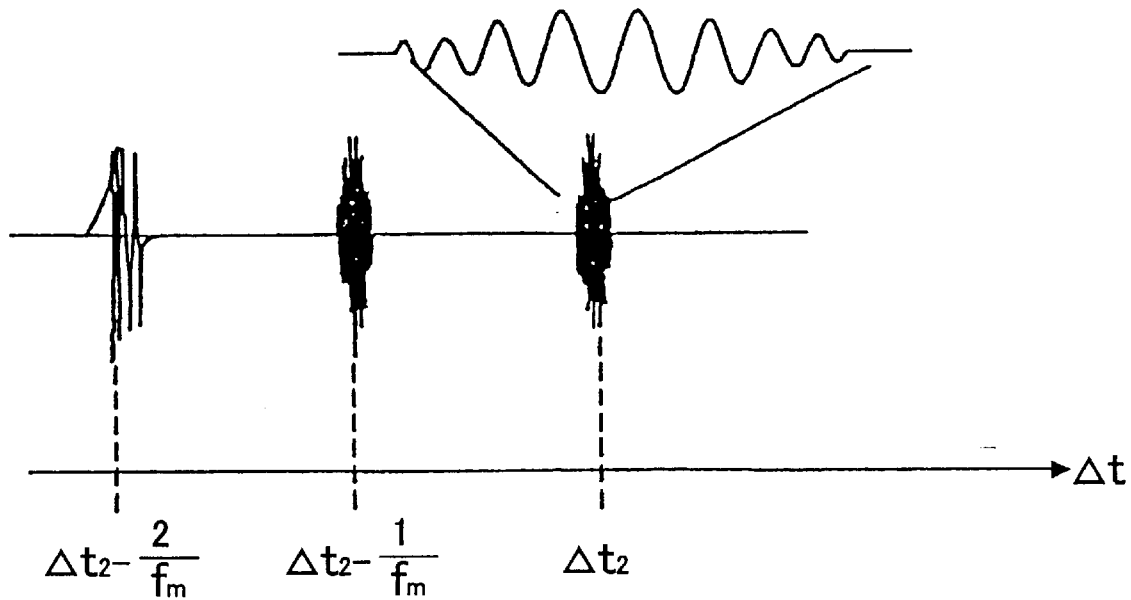
FIG. 5 shows a time—voltage characteristic of a light detection signal.

As the first optical frequency comb generator 5 and second optical frequency comb generator 6 have the same performance, the product of $A_k$ and $B_k*$ is a real number. Accordingly, when $2\pi f_m \Delta t_2 - \phi$ in the above formula (4) is 0 or integer times of $2\pi$, the modulated waveform in the vicinity of a frequency of Sf becomes very large. That is, the modulated waveform appears, as shown in FIG. 5, at the time of $\Delta t_2 + (N/f_m)$ (N is an integer) according to the change in the time difference $\Delta t$, as a result of the phase shift amount $\phi$ being changed.

The control part 15 changes the time difference $\Delta t$ by changing the phase shift amount $\phi$, and obtains the time difference $\Delta t_2$. Then, the control part 15 determines the reflection point inside the measurement sample S. Thereby, the control part 15 obtains the reflectance distribution signal for the inside of the measurement sample S, and obtains correspondence relationship between the reflection points.

Further, the control part 15 uses the light detection signal given by the photodetector 13, thus obtains spectrum information, and thus can know material and so forth of the measurement sample S.

In the tomograph apparatus 1 shown in FIG. 1, the phase shifter 17 is provided for providing the second modulation signal after giving the phase difference thereto, to the second optical frequency comb generator 6, for example. However, it is also possible to shift the phase of the first modulation signal provided to the first optical frequency comb generator 5.

Further, when the tomography apparatus 1 merely measures the correspondence relationship between the reflection points of the measurement sample S, it is not necessary to be limited to the example in which the frequency shifter 8 shown in FIG. 1 gives the frequency shift to the light provided from the mirror 7. It is also possible that the frequency shifter 8 is disposed preceding to the first optical frequency comb generator 5, or the like. Further, it is also possible to omit the frequency shifter 8.

Figure 6:
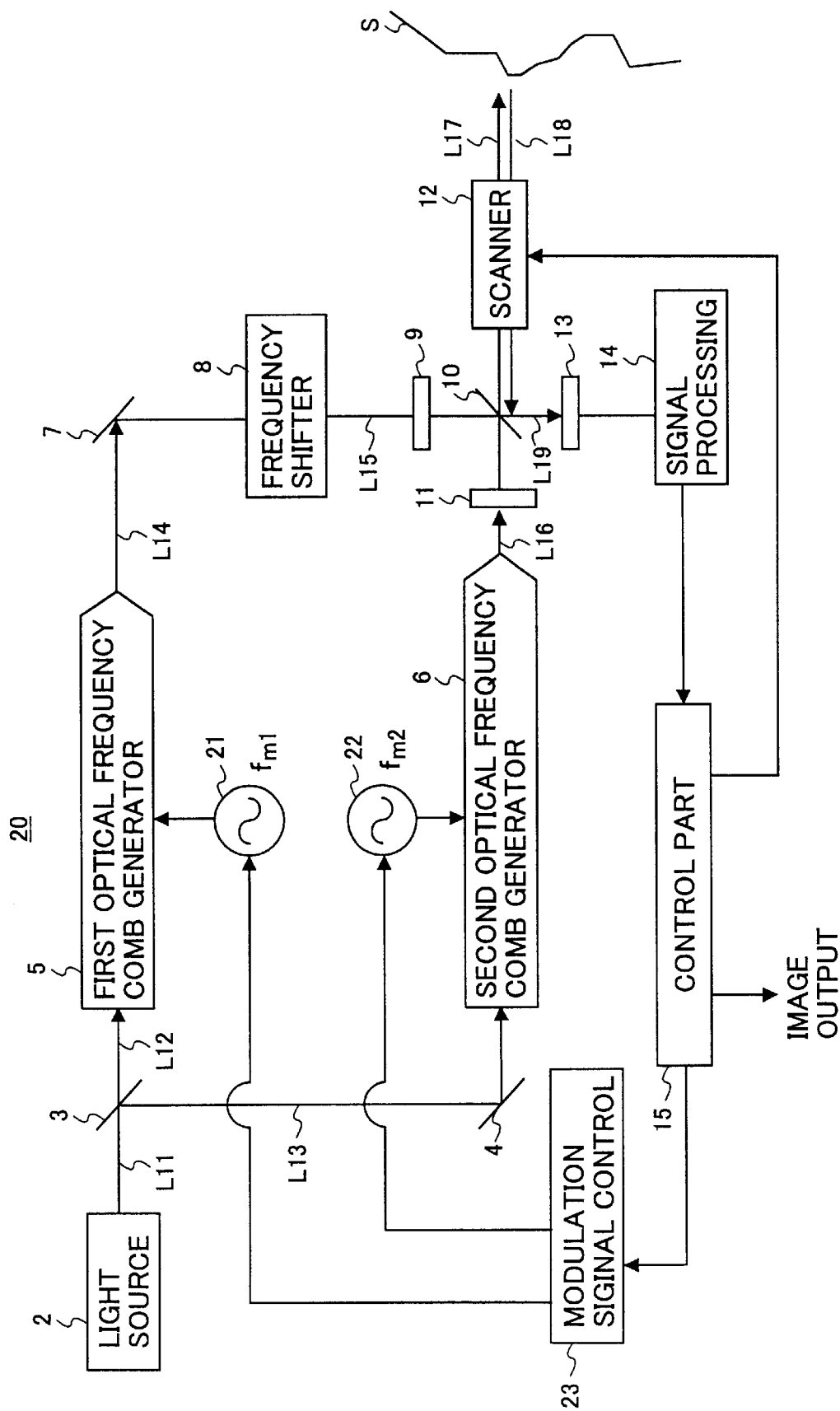
FIG. 6 is a block diagram showing a configuration of another tomography apparatus to which the present invention is applied.

Another tomography apparatus 20 to which the present invention is applied will now be described with reference to FIG. 6. As the same reference numerals are given to the same components as those of the above-described tomography apparatus 1, detailed description thereof is omitted.

The tomography apparatus 20 is different from the tomography apparatus 1 shown in FIG. 1 in that a first external oscillator 21 providing a first modulation signal to the first optical frequency comb generator 5, a second external oscillator 22 providing a second modulation signal to the second optical frequency comb generator 6, and a modulation signal control part 23 controlling the first external oscillator 21 and second external oscillator 22, are provided.

Figure 7:
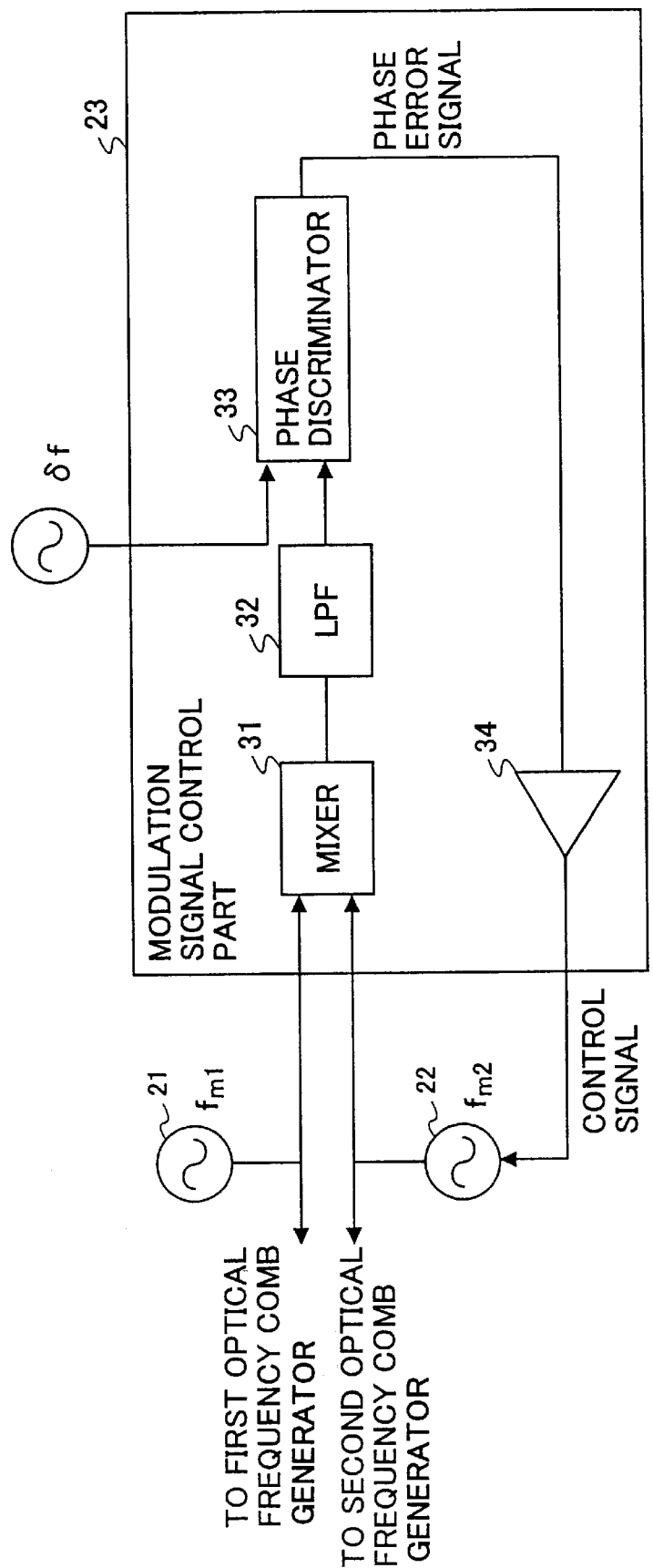
FIG. 7 is a block diagram showing a configuration of a modulation signal control part of the other tomography apparatus to which the present invention is applied.

The modulation signal control part 23 includes, as shown in FIG. 7, a mixer 31, a low-pass filter 32, a phase discriminator 33 and a control amplifier 34. In this modulation signal control part 23, the modulation signals output from the first external oscillator 21 and second external oscillator 22 are mixed by the mixer 31, and then input to the phase discriminator 33 via the low-pass filter 32. The phase discriminator 33 uses an oscillation signal δf given by the control part 15 as a reference signal, and generates a phase error signal which is in proportion to a phase difference between the signal provided from the low-pass filter and the reference signal. This modulation signal control part 23 outputs the phase error signal generated by the phase discriminator 33 to the external oscillator 22 via the control amplifier 34. Thereby, the modulation signal control part 23 performs heterodyne phase synchronization control on the first external oscillator 21 and second external oscillator 22, thus, controls the phase difference between the first modulation signal $f_{m1}$ and second modulation signal $f_{m2}$ generated by the first external oscillator 21 and second external oscillator 22 at a high accuracy, and generates the first modulation signal $f_{m1}$ and second modulation signal $f_{m2}$ having different frequencies.

Then, a fact that continues change in phase shift amount φ corresponds to that the frequency $f_{m1}$ and frequency $f_{m2}$ are different from one another, and $$f_{m2} - f_{m1} = \delta f \tag{5}$$

will now be described.

In FIG. 1, the laser light L3 is incident on the second optical frequency comb generator 6 from the beam splitter 3, and, also, the second modulation signal having a voltage $V = \sin(2\pi f_m t + \phi)$ is input thereto from the phase shifter 17. At this time, when $\phi = 2\pi\delta ft$, the second modulation signal becomes $$V = \sin(2\pi(f_m + \delta f)t)$$

and, thus, becomes the signal having a frequency $f_m + \delta f$. Accordingly, it is possible to change the phase difference φ through a wider range by using the two oscillators 21 and 22 than that in use of the phase shifter 17. Thus, in the tomography apparatus 20 shown in FIG. 6, it is possible to perform sweeping of the phase difference through a wider range in comparison to the above-described tomography apparatus 1.

The first external oscillator 21 provides the first modulation signal of the frequency $f_{m1}$ to the first optical frequency comb generator 5. Further, the second external oscillator 22 provides the second modulation signal of the frequency $f_{m2}$ different from the frequency $f_{m1}$ to the second optical frequency comb generator 6. The first external oscillator 21 and second external oscillator 22 control the frequency difference between the first modulation signal and second modulation signal according to the control signal given by the modulation signal control part 23. As a result, the reference light L14 and object light L16 are output depending on the time difference expressed by $\Delta t = \delta ft/fm$.

In this tomography apparatus 20, the control part 15 controls the frequency $f_{m1}$ and frequency $f_{m2}$ so as to control the time difference Δt of interference timing between the reference light and object light, detects interference between the reference light and object light, generates the reflectance distribution signal along the depth directions of the measurement sample S, also, obtains spectrum information by performing spectrum analysis using the light detection signal detected by the photodetector 13, and observes the material of the measurement sample S.

Figure 8:
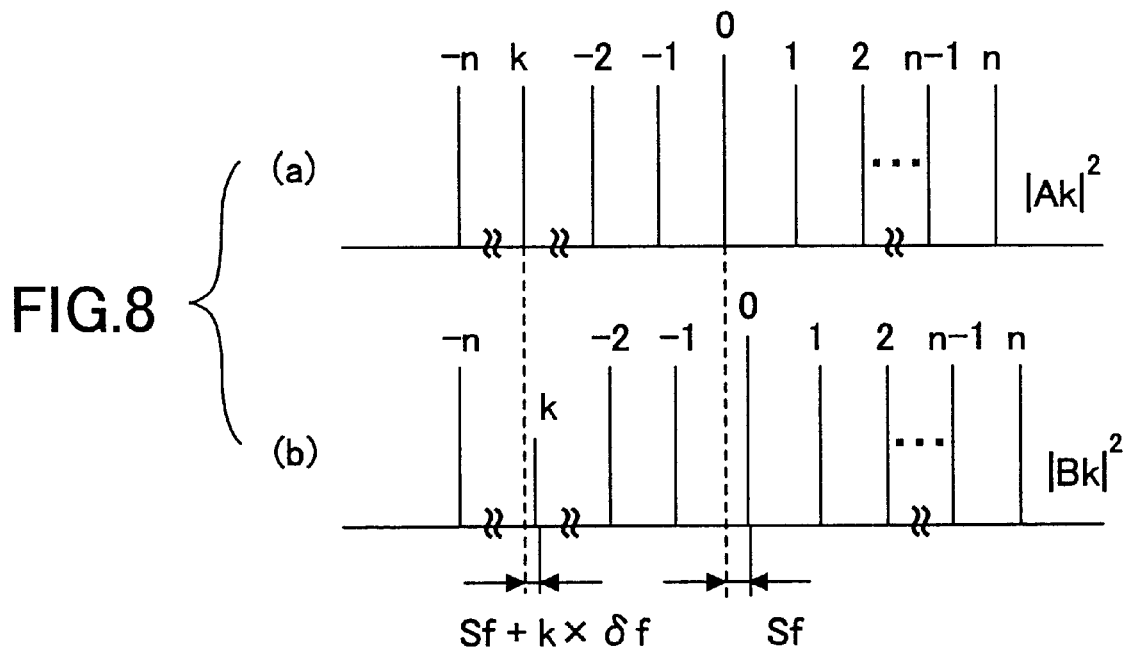
FIG. 8 (a) shows a power spectrum of the reference light and (b) shows a power spectrum of interference light.
Figure 9:
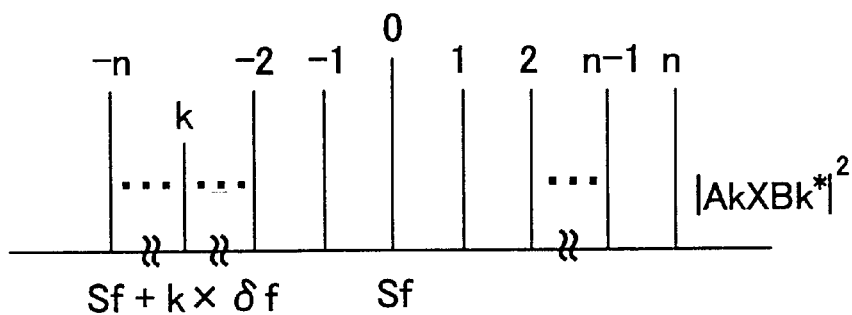
FIG. 9 shows a power spectrum of a light detection signal detecting the interference light.

That is, when the power spectrum of the reference light having undergone negative frequency shift given by the first optical frequency comb generator 5 has the characteristics shown in FIG. 8(a) and the power spectrum of the object light has the characteristics shown in FIG. 8(b), for example, and when the control part 15 performs spectrum decomposition processing on the light detection signal detecting the interference light through the photodetector 13, and thus measures the power spectrum, the amplitude $A_k B_k^*$ of the sideband of the k-th light of the first optical frequency comb generator 5 and second optical frequency comb generator 6 is obtained as the value for the frequency (Sf+kδf), and it is used as the spectrum information. For example, when absorption occurs for the k-th light component of the object light as shown in FIG. 8(b), the spectrum information such that the k-th signal component detected by the photodetector 13 is reduced in signal intensity, as shown in FIG. 9.

Further, in this tomography apparatus 20, as the modulation signal control part 23 performing the heterodyne control so as to generate the first modulation signal and second modulation signal, it is possible to control the phase difference between the first modulation signal and second modulation signal at a high accuracy, and obtain the interference result and spectrum information with a high accuracy. Further, in this tomography apparatus 20, it is possible to control the phase difference at a high accuracy while the phase difference is caused to sweep through a wide range.

A principle of the tomography apparatuses 1 and 20 to which the present invention is applied will now be described.

In the tomography apparatuses 1 and 20, the interference timing between the reference light and object light emitted from the first optical frequency comb generator 5 and second optical frequency comb generator 6 is controlled. Thereby, the interference is caused to occur between the reference light and object light having the sidebands. This matter is proved by reference to an experimental system shown in FIG. 10.

Figure 10:
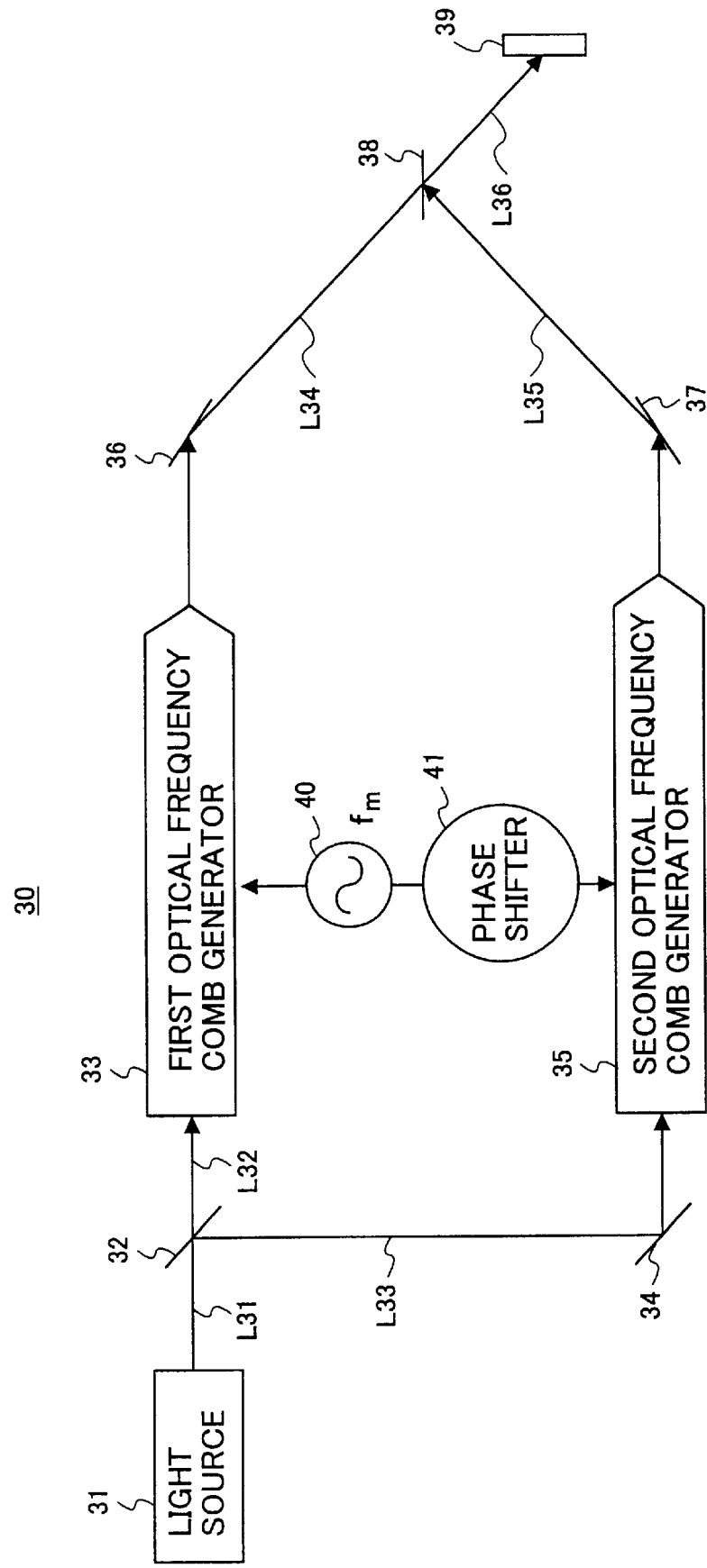
FIG. 10 is a block diagram showing a configuration of an experimental system for illustrating a principle of a tomography apparatus to which the present invention is applied.

In this experimental system shown in FIG. 10, laser light L31 emitted from a light source 31 is split by a beam splitter 32, thereby, laser light L32 is incident on a first optical frequency comb generator 33, and, also, laser light L33 is incident on a second optical frequency comb generator 35 via a mirror 34. Then, the laser light L32 and L33 incident on the first optical frequency comb generator 33 and second optical frequency comb generator 35 have sidebands generated, is caused to be reference light L34 and object light L35, are emitted therefrom while timing thereof is controlled, and are incident on a photodetector 39 via mirrors 36, 37, and a beam splitter 38. There, the reference light L34 and object light L35 are combined by the beam splitter 38, thereby, are caused to be interference light L36, and is incident on the photodetector 39.

Further, an external oscillator 40 providing a first modulation signal of a frequency $f_m$ to the first optical frequency comb generator 33 and a phase shifter 41 shifting the phase of the first modulation signal provided by an external oscillator and providing a second modulation signal of the frequency $f_m$ to the second optical frequency comb generator 35 are included in the experimental system 30. In this experimental system 30, same as the above-described tomography apparatuses 1 and 20, the phase difference of the phase shift amount φ is provided between the first modulation signal and second modulation signal, and the time difference Δt of the interference timing is controlled.

Figure 11:
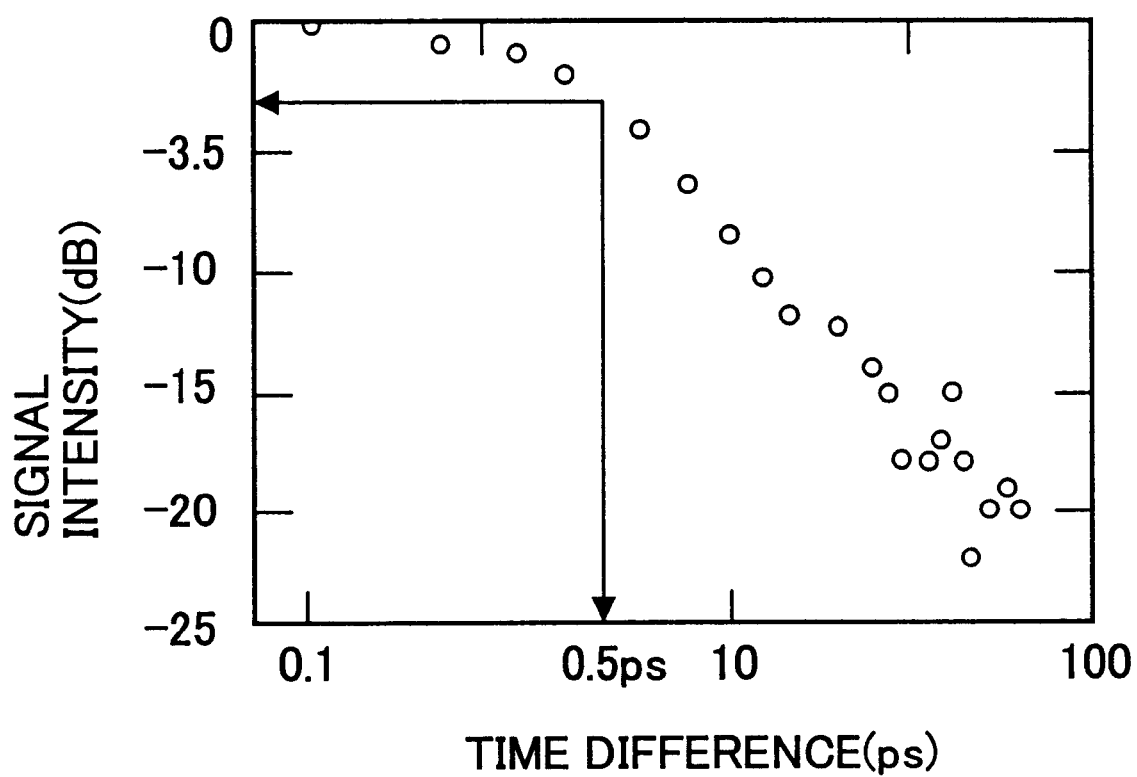
FIG. 11 shows a change of an intensity (dB) of the interference light obtained when the time difference $\Delta t$ (ps) is changed in the experimental system shown in FIG. 9.

FIG. 11 shows a result of measurement of a signal intensity (dB) of a light detection signal when the interference light L36 is detected by the photodetector 39 when, in this experimental system 30, the time difference Δt (ps) is changed as a result of timing between the reference light L34 and object light L35 being changed.

According to FIG. 11, it can be seen that the signal intensity is large when the time difference Δt is in a range 0 (ps) through 0.5 (ps), and the signal intensity becomes smaller gradually as the time difference Δt becomes further larger. From this result, it can be seen that, the interference of light occurs between the reference light and object light provided from the first optical frequency comb generator 33 and second optical frequency comb generator 35, and, same as a case where a light intensity of interference light is measured as a difference in light path is changed between the reference light and object light, the interference can be measured according to the coherent distance determined from a difference in spectrum between the reference light L34 and object light L35. Accordingly, it is proved that, by using light from the independent two first optical frequency comb generator 33 and second optical frequency comb generator 35, the light intensity of interference light changes.

In the tomography apparatus in the prior art, it was not possible to electrically control the interference position when using the light source made of LED (Light Emitting Diode), and, also, this was not possible even when using two independent pulse light sources.

However, in the tomography apparatuses 1 and 20 to which the present invention is applied, because the single single-mode laser having high coherence is used in common, it is possible to always cause the interference of light to occur at the position at which the pulses coincide, although the timing of the reference light and object light is controlled by the first optical frequency comb generator 5 and second optical frequency comb generator 6, although using a wide spectrum range such as that generated by a mode lock laser.

Further, in the tomography apparatuses 1 and 20, the interference timing is controlled as a result of the phase difference between the first and second modulation signals provided to the first optical frequency comb generator 5 and second optical frequency comb generator 6 being changed. Accordingly, it is possible to provide the time difference between the reference light and object light only through electric control, and to detect the interference position by sweeping of the time difference Δt at high speed. That is, in the tomography apparatuses 1 and 20, there is no necessity of performing mechanical modulation of the mirror for the reference light in order to provide a difference in light path (time difference) between the reference light and object light as in the tomography apparatus in the prior art. Accordingly, the sweeping speed is not limited by a mechanical speed.

Further, in the tomography apparatus in the prior art, the mirror for the reference light is used for giving the frequency shift for each component of light spectrum through Doppler shift. There, assuming that a speed of mechanically driving the mirror for the reference light is represented by v, the Doppler shift performed on the reference light when it is incident on the mirror for the reference light perpendicularly and is reflected thereby is expressed by $$2\nu v/c \text{ (Hz)}$$

In the above formula, ν denotes the frequency of the reference light, and c denotes the velocity of light. Accordingly, from the above formula, the difference of Doppler shift for 1 Hz of frequency interval in mode of light is $$2v/c \text{ (Hz/Hz)}$$

For example, assuming that the mechanical speed of driving the mirror for the reference light is 300 m/s (velocity of sound), the Doppler shift is $2 \times 10^{-6}$ Hz.

On the other hand, in the tomography apparatuses 1 and 20 to which the present invention is applied, it is possible to cause the frequency shift to occur to the necessary amount for each frequency component of the reference light. Accordingly, in the tomography apparatuses 1 and 20, it is not necessary to perform mechanical operation, but it is possible to cause the frequency shift to occur equivalent to the Doppler shift. That is, in the tomography apparatuses 1 and 20, the first optical frequency comb generator 5 and second optical frequency comb generator 6 are used instead of the light source of low coherence in the prior art, the frequency shift for each frequency component of the light emitted therefrom is used, and the frequency shift to the necessary amount for each frequency component is caused to occur. Thereby, by causing the relative frequency shift for each frequency component included in the reference light and object light to occur, it is possible to perform the processing which is performed through mechanical operation in the prior art, only through electric control.

In the tomography apparatuses 1 and 20, assuming that the modulation frequency of the first optical frequency comb generator 5 emitting the object light is indicated by fm and the modulation frequency of the second optical frequency comb generator 6 emitting the reference light is indicated by $f_m+\delta f$, the difference of the frequency shift for 1 Hz of frequency of light is $\delta f/f_m$ (Hz/Hz). For example, assuming that the frequency difference δf between the first optical frequency comb generator 5 and second optical frequency comb generator 6 is $1 \times 10^6$ (Hz) and the modulation frequency $f_m$ is $1 \times 10^9$ (Hz), the frequency difference (Hz/Hz) is $1 \times 10^{-3}$ (Hz/Hz). Accordingly, in the tomography apparatuses 1 and 20, it is possible to obtain the frequency difference for 1 Hz 500 times the one ($2 \times 10^{-6}$ (Hz)) obtained when the mechanical driving in the prior art is used. Accordingly, in the tomography apparatuses 1 and 20, it is possible to obtain the sweeping speed 500 times the one obtained in the tomography apparatus in the prior art for the depth directions of the measurement sample S. Further, as it is not practical in the tomography apparatus in the prior art to perform the mechanical operation at the velocity of sound, the sweeping speed in the tomography apparatuses 1 and 20 is further higher than that in the tomography apparatus in the prior art.

Further, according to the tomography apparatuses 1 and 20, as the electric sweeping of time difference is performed, it is possible to provide the frequency shift more precisely than in the tomography apparatus in the prior art employing the mechanical operation. Accordingly, it is possible to perform calibration of distance precisely.

Furthermore, according to the tomography apparatuses 1 and 20, as the electric sweeping of time difference is performed, it is possible to freely select the sweeping range in the depth direction of the measurement sample S.

Furthermore, in the tomography apparatuses 1 and 20, although performing the frequency shift, because the frequency interval of light emitted from the first optical frequency comb generator 5 and second optical frequency comb generator 6 is discrete, the value of the relative phase between the sidebands returns to the original one each of the time of 1/δf. Accordingly, according to the tomography apparatuses 1 and 20, it is not necessary to perform a reciprocating motion of the reference mirror which is performed in the tomography apparatus in the prior art employing the mechanical operation. Thereby, it is possible to perform the measurement of the interference position precisely even when the frequency shift is performed successively at high speed.

In the tomography apparatuses 1 and 20, as shown in FIG. 11, the time difference which can be provided between the reference light and object light is 0.5 (ps), corresponding to the resolution on the order of 0.15 mm in distance. However, by employing recent optical frequency comb generators having a higher performance, or employing optical frequency comb generators using optical fibers, it is possible to further improve the resolution.

Further, for the tomography apparatuses 1 and 20, although the case has been described where the comb generators have the same performance, the present invention can be applied as long as the comb generators have the same function of controlling the phase.

Further, for the present invention, the case where the optical frequency comb generators are used as the pulse light sources has been described. However, it is possible to obtain the effect same as that described above by controlling the central frequency of each mode and the cycle frequency of a pulse light source such as a mode-locked laser or the like so as to imitatively produce the light emitted from the optical frequency comb generator.

Further, in the tomography apparatuses 1 and 20 shown in FIG. 1, it is possible that the respective configuration parts including the first and second optical frequency comb generators are those employing optical fibers, and, also, are concerted by using optical fibers. In description made below for a tomography apparatus, detailed description is omitted by giving the same reference numerals.

Figure 12:
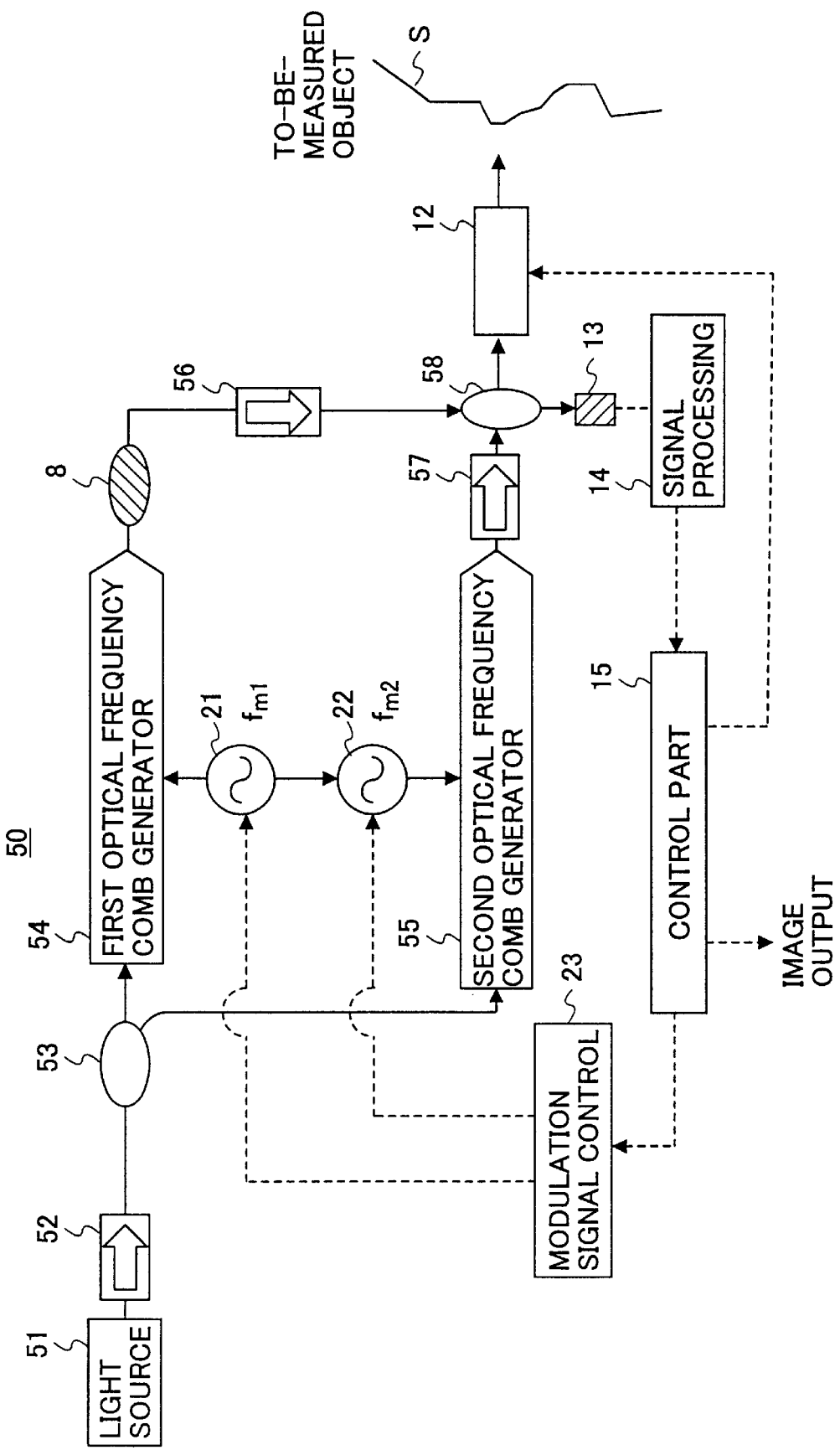
FIG. 12 is a block diagram showing a configuration of another tomography apparatus to which the present invention is applied.

In this tomography apparatus 50, as shown in FIG. 12, a light source 51, an isolator 52, and a coupler 53 are provided. Laser light split by the coupler 53 is incident on a first optical frequency comb generator 54 and a second optical frequency comb generator 55. The first optical frequency comb generator 54 and second optical frequency comb generator 55 generate the sidebands in the light provided from the coupler 53 via optical fibers, and emit the light to a coupler 58 via an isolator 56, and emit the light to the light to the coupler 58 via an isolator 57. The coupler 58 emits the light provided from the first optical frequency comb generator 54 to a measurement sample S via a scanner 12, combines the object light reflected by the measurement sample S and the reference light provided from the second optical frequency comb generator 55, and emits the combined light to a photodetector 13. The isolators 52, 56 and 57 have functions of blocking the light returning from the couplers 53 and 58.

In this tomography apparatus 50, the light source 51, isolator 52, coupler 53, first optical frequency comb generator 54, phase shifter 8, isolator 56, scanner 12, coupler 58 and photodetector 13 are connected by optical fibers. Also, the coupler 53, second optical frequency comb generator 55, isolator 57 and coupler 58 are connected by optical fibers. Thereby, in comparison to the tomography apparatuses 1 and 20, it is possible to reduce the size of the entirety of the apparatus.

Figure 13:
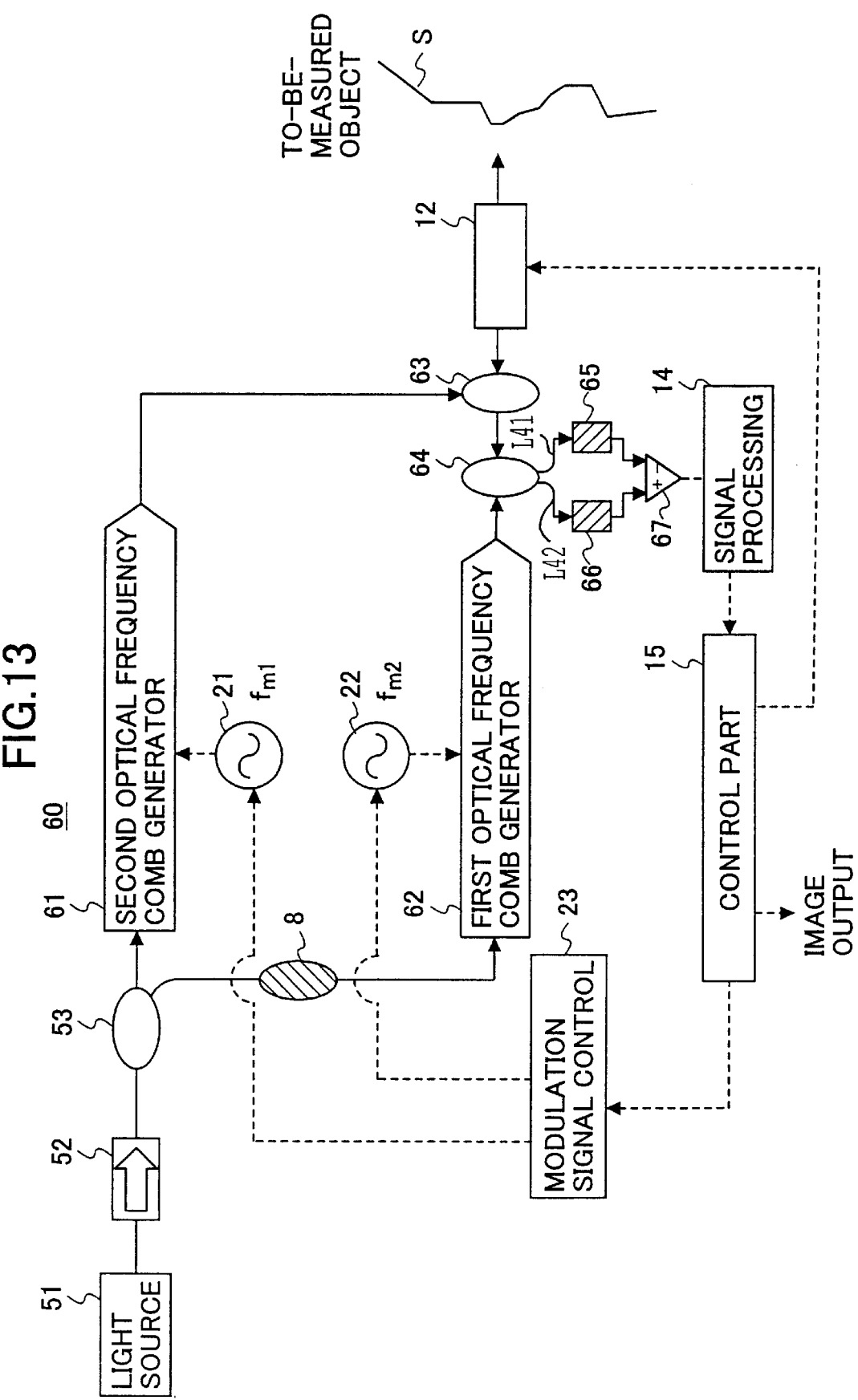
FIG. 13 is a block diagram showing a configuration of another tomography apparatus to which the present invention is applied.
Figure 14:
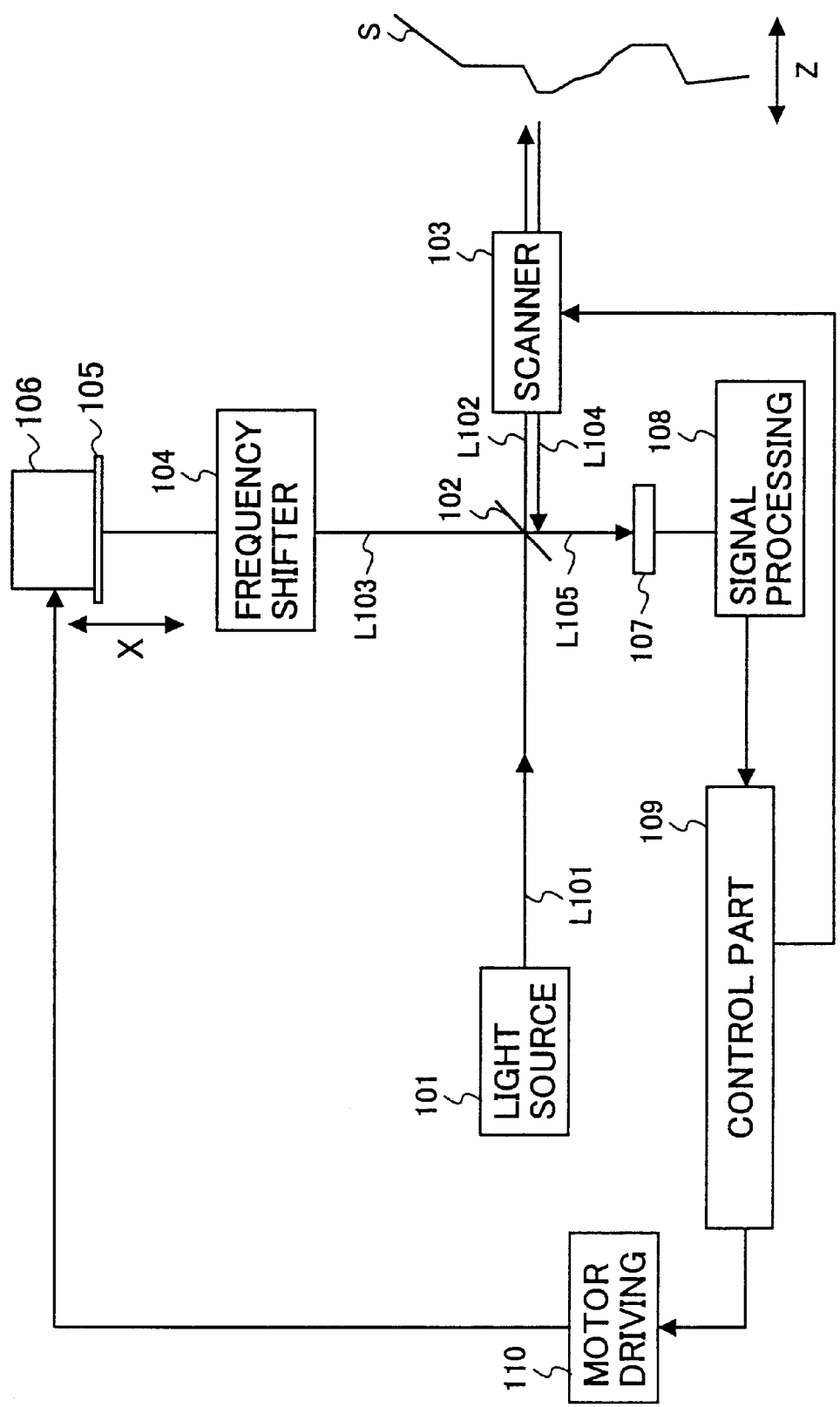
FIG. 14 is a block diagram showing a configuration of a shape detecting apparatus in the prior art.

Further, another tomography apparatus 60 in which optical components are connected by using optical fibers is shown in FIG. 13. In this tomography apparatus 60, the object light emitted from a first optical frequency comb generator 61 is incident on the measurement sample S via an optical circulator 63 and a scanner 12, and, then, the object light reflected by the measurement sample S is incident on a 50% coupler 64 via the optical circulator 63.

The optical circulator 63 causes the light provided from the second optical frequency comb generator 61 to pass therethrough with an optical efficiency of 100% toward the scanner 12, and transmits the light provided from the scanner 12 toward the 50% coupler 64. That is, the optical circulator 63 does not reflect the incident light in the incident direction of the light, but transmits it.

The 50% coupler 64 combines the object light provided from the optical circulator 63 and the reference light provided from the first optical frequency comb generator 62, and emits the light to a first photodetector 65 and a second photodetector 66 as the light of 50% of the light quantity of all the interference light.

The first photodetector 65 and second photodetector 66 output detection signals in accordance with the light intensities of the light provided by the 50% coupler 64, to a differential amplifier 67.

The differential amplifier 67 has the detection signal provided by the second photodetector 66 input to a positive input terminal thereof, and has the detection signal provided by the first photodetector 65 input to a negative input terminal thereof. This differential amplifier 67 obtains a difference between the detection signals provided by the first photodetector 65 and second photodetector 66, thereby reduces the noise, and supplies the interference detection signal to a signal processing part 14.

In this tomography apparatus 60, by obtaining the difference in signal intensity between the detection signals generated from the object light L41 and reference light L42 detected by the first photodetector 65 and second photodetector 66, it is possible to improve the S/N ratio of the interference detection signal by reducing the influence of intensity noise.

Further, in this tomography apparatus 60, because the optical circulator 63 is used, the light incident on the coupler 58 is not reflected thereby in the incident direction of the light as in the above-described tomography apparatus 50. Accordingly, it is possible to reduce the optical loss due to the coupler, to reduce the waste of light, and, in comparison to the tomography apparatus 50, it possible to achieve improvement in S/N ratio.

As described above, according to the interference detecting apparatus according to the present invention, a controlling means is provided, and it is possible to control the timing of emission between the reference light from a first optical frequency comb generating means and the object light from a second optical frequency comb generating means, and to detect the interference of interference light. Accordingly, it is possible to electrically perform the sweep of emission timing between the reference light and object light, to achieve high-speed operation of the detecting of the interference position, and to perform measurement of a sample within a short time.

Further, according to the interference detecting apparatus according to the present invention, a controlling means is provided, and it is possible to control the timing of emission between the reference light from a first optical frequency comb generating means and the object light from a second optical frequency comb generating means, and to detect the interference of interference light. Accordingly, it is possible to electrically perform the sweep of the emission timing between the reference light and object light, to achieve high-speed operation of detecting of the interference position, and to shorten the processing time required for generating an image representing the shape of a sample.

Further, embodiments of the present invention are not limited to those described above, and variations and modifications may be made without departing from the scope of the present invention.

The present application is based on Japanese priority application No. 2000-46831, filed on Feb. 18, 2000, the entire contents of which are hereby incorporated by reference.

What is claimed is:

1. An interference detecting apparatus, comprising:
   a light source emitting light having coherency;
   a first signal generating means generating a first signal having a frequency of $f_1$;
   a first optical frequency comb generating means using the first signal provided from said first signal generating means, and modulating the light provided from said light source, so as to generate reference light having a sideband every interval of frequency $f_1$ in the light provided from said light source;
   a second signal generating means generating a second signal having a frequency of $f_2$;
   a second optical frequency comb generating means using the second signal provided from said second signal generating means, and modulating the light provided from said light source, so as to generate object light having a sideband every interval of frequency $f_2$ in the light provided from said light source;
   a combining means combining the reference light provided from said first optical frequency comb generating means and the object light generated by said second optical frequency comb generating means and reflected by a to-be-measured object so as to generate interference light; and
   a detecting means controlling interference timing between the reference light provided from said first optical frequency comb generating means and the object light provided from said second optical frequency comb generating means, by using a phase difference or frequency difference between the first signal and second signal, and detecting a change in light intensity of the interference light.

2. A tomography apparatus, comprising:
   a light source emitting light having coherency;
   a first signal generating means generating a first signal having a frequency of $f_1$;
   a first optical frequency comb generating means using the first signal provided from said first signal generating means, and modulating the light provided from said light source, so as to generate reference light having a sideband every interval of frequency $f_1$ in the light provided from said light source;
   a second signal generating means generating a second signal having a frequency of $f_2$;
   a second optical frequency comb generating means using the second signal provided from said second signal generating means, and modulating the light provided from said light source, so as to generate object light having a sideband every interval of frequency $f_2$ in the light provided from said light source;
   a combining means combining the reference light provided from said first optical frequency comb generating means and the object light generated by said second optical frequency comb generating means and reflected by a to-be-measured object so as to generate interference light;
   a first detecting means controlling interference timing between the reference light provided from said first optical frequency comb generating means and the object light provided from said second optical frequency comb generating means, by using a phase difference or frequency difference between the first signal and second signal, and detecting a change in light intensity of the interference light;
   a scanning means scanning the to-be-measured object with an incident position of the object light provided from said second optical frequency comb generating means;
   a second detecting means detecting shape information of the to-be-measured object based on a interference detection result given by said first detecting means; and
   an image producing means producing an image representing a shape of the to-be-measured object by using a plurality of shape information sets of the to-be-measured object generated by said second detecting means as a result of scanning by said scanning means.

3. The tomography apparatus as claimed in claim 2, further comprising:
   a third detecting means detecting spectrum information by using the result of interference detection detected by said first detecting means.

4. The tomography apparatus as claimed in claim 2, comprising:
   a heterodyne control means performing heterodyne phase synchronization control of the first signal and second signal to be generated by said first signal generating means and second signal generating means.

5. The tomography apparatus as claimed in claim 2, wherein said first optical frequency comb generating means and second optical frequency comb generating means use optical fibers, and the respective means are connected by using optical fibers.

* * * * *